US00PP29603P2

(12) United States Plant Patent
Hansen

(10) Patent No.: US PP29,603 P2
(45) Date of Patent: Aug. 14, 2018

(54) ***PENSTEMON* PLANT NAMED 'MIDNIGHT MASQUERADE'**

(50) Latin Name: *Penstemon digitalis*
Varietal Denomination: Midnight Masquerade

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/731,994

(22) Filed: Sep. 5, 2017

(51) Int. Cl.
*A01H 5/02* (2018.01)

(52) U.S. Cl.
USPC ..... Plt./465

(58) Field of Classification Search
USPC ..... Plt./465
See application file for complete search history.

*Primary Examiner* — Annette H Para

(57) ABSTRACT

The new and distinct cultivar of ornamental, winter-hardy, beardtongue plant, *Penstemon* 'Midnight Masquerade' with strictly upright, tightly-compact strong stems, strong purple flowers for about four weeks and dark purple foliage that retains its coloration through the season. Useful in the landscape as a specimen plant, en masse or container plant, and attractive to hummingbirds.

1 Drawing Sheet

Botanical classification: *Penstemon digitalis.*
Variety denomination: 'Midnight Masquerade'.

BACKGROUND OF THE INVENTION

The present invention relates to a new and distinct plant of beardtongue, botanically known as *Penstemon* 'Midnight Masquerade' and will be referred to hereinafter also by its cultivar name 'Midnight Masquerade' and as the new plant. The new plant cultivar of beardtongue is a hardy herbaceous perennial grown for landscape use.

*Penstemon* 'Midnight Masquerade' is a seed selection derived from second generation selfed *Penstemon* 'Pocahontas' U.S. Plant Pat. No. 24,804 collected by the inventor in the fall of 2014 at a wholesale perennial nursery in Zeeland, Mich. All subsequent evaluations were performed in a full-sun trial garden at the same nursery with loamy sand soil and irrigation and fertilizer as required. The single seedling plant was selected for further evaluation during the summer of 2015. The new plant was propagated by basal shoot cuttings at the same nursery in Zeeland, Mich., and the original plant and the cuttings evaluated over the next two years until final approval for introduction in the summer of 2015. The resultant asexually propagated cuttings have been stable and identical to the original plant in successive asexual propagations.

No plants of *Penstemon* 'Midnight Masquerade' have been sold or disclosed in this country, or anywhere in the world, by this or any name, more than one year prior to the filing of this application, with the exception of that which was sold or disclosed either directly or indirectly from the inventor.

SUMMARY OF THE INVENTION

*Penstemon* 'Midnight Masquerade' differs from its parent as well as all other hardy beardtongue known to the inventor in a combination of traits. The following characteristics in combination distinguish 'Midnight Masquerade' from all other beardtongue plants known to the inventor:

1. Strictly upright growth with tightly-compact strong stems;
2. Foliage developing and maintaining dark purple coloration in high light intensity;
3. Flowering with strong purple horizontal flowers for four weeks beginning early summer in Michigan.

The nearest comparison cultivars are *Penstemon* 'Blackbeard' U.S. Plant patent application Ser. No. 15/530,316, 'Pocahontas' U.S. Plant Pat. No. 24,804 and 'Dark Towers' U.S. Plant Pat. No. 20,013. The new plant has flowers that are a deeper shade of light purple and the habit is shorter than either 'Pocahontas', 'Blackbeard' or 'Dark Towers'. Compared with 'Dark Towers' the new plant is more compact and shorter in habit, and slightly shorter and more compact than 'Blackbeard'. 'Midnight Masquerade' is slightly shorter in habit than all of the above plants.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a two-year-old plant grown in full sun field in loamy sand soil in trial gardens of a nursery in Zeeland, Mich.

DETAILED BOTANICAL DESCRIPTION

Figure 1:
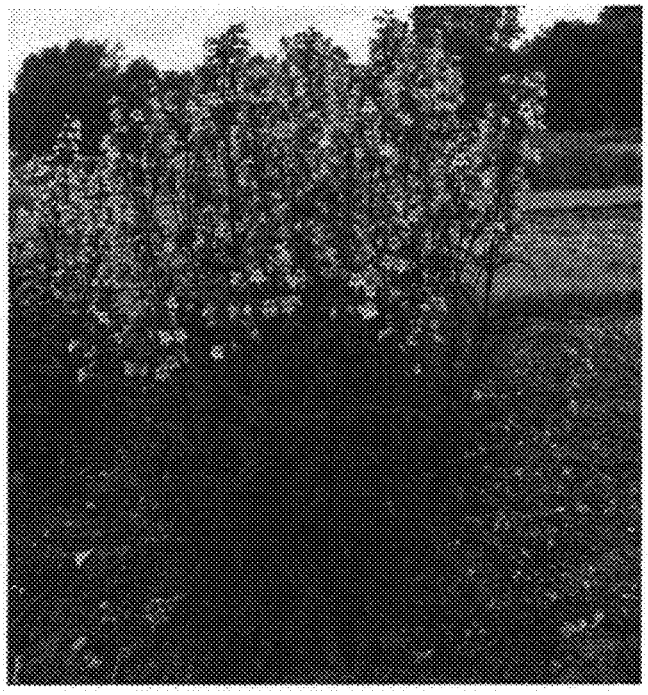
FIG. 1 shows 'Midnight Masquerade' in the landscape in peak flower with very dark foliage.
Figure 2:
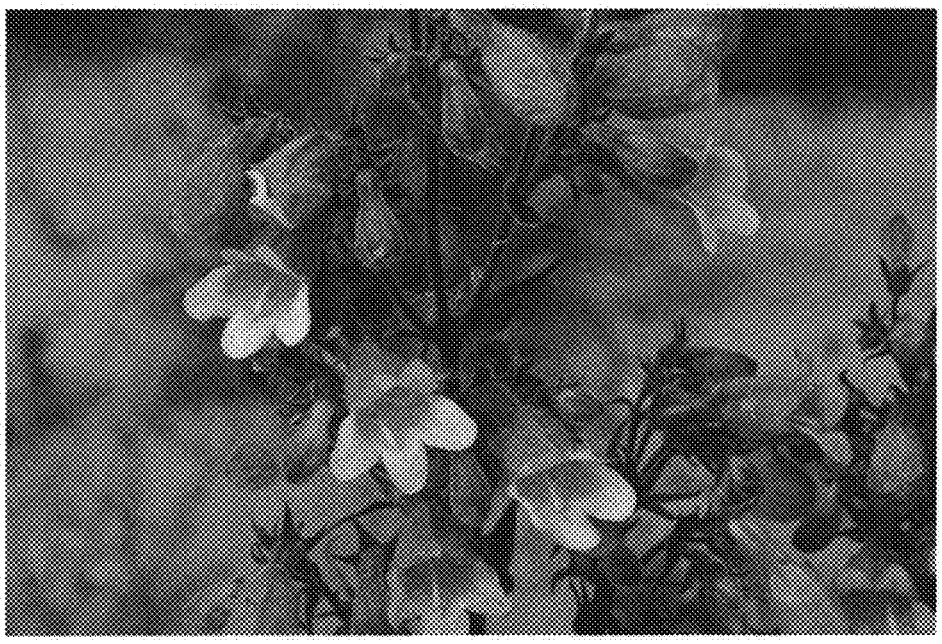
FIG. 2 shows a close-up of the flowers and buds of 'Midnight Masquerade'.

The following is a detailed description of *Penstemon* 'Midnight Masquerade' as observed and compared to other cultivars for two years in trial gardens and production fields at a nursery in Zeeland, Mich. The following description is of a one-year-old plant of *Penstemon* 'Blackbeard' in a full-sun display garden in Zeeland, Mich. with limited supplemental fertilizer and irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2015 edition of The R.H.S. Colour Chart of The Royal Horticultural Society, London, England, except where common dictionary color terms are used.

Parentage: The female (seed) parent is a selection of selfed 'Pocahontas' and the male (pollen) parent was the same selection of selfed 'Pocahontas';

Plant habit: Herbaceous winter-hardy, perennial with upright rigid stems emerging from the base in the spring; up to about 15 stems per plant; flowering in branched panicle;

Plant size: About 82.0 cm in height, average stem 78.0 cm tall, and about 65.0 cm in width about 60 cm above soil;

Root description: Fibrous, well-branched, developing to thickness of about 1.0 mm; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 4 liter pot from rooted plug;

Stem description: Terete; oppositely branched in distal region; glabrous; lustrous; average about 80.0 cm long and about 7.0 mm across near base;

Stem color: Variable between RHS 187A and RHS 187B;

Internode: Average about 10 per stem, average internode length about 5.5 cm, larger toward flowers;

Internode color: Same as surrounding stem;

Foliage description: Simple; typically opposite; basal leaves oblanceolate to ovate, decumbent, acute apex, sessile attenuate base, margin serrate; cauline leaves lanceolate, narrowly acute apex, with sessile, truncate, clasping base; margin serrate, teeth more pronounced on cauline leaves than basal leaves; abaxial and adaxial surface glabrous, slightly lustrous adaxial and matte abaxial; fragrance not detected;

Leaf size: Basal leaves to about 18.0 cm long and about 7.2 cm wide; cauline leaves to about 16.0 cm long and about 4.8 mm wide; size decreasing distally; average size about 12.1 cm long and about 3.4 cm wide;

Leaf color: Young expanding adaxial nearest RHS 187A, abaxial blend between RHS N186C and RHS 187A; mature adaxial nearest RHS 187A with slight undertone of nearest 137A, abaxial blotchy nearest RHS 137B with blush of nearest RHS N187C;

Leaf venation: Pinnate;

Vein color: Young abaxial midrib nearest RHS 158C with slight blush of nearest RHS 70B in basal 1.0 cm then distal one-third to one-half RHS 187C, young abaxial secondary veins RHS 187C; young adaxial midrib nearest RHS N186D, secondary veins nearest RHS 187C; mature abaxial and adaxial midrib and secondary veins nearest RHS 187A;

Petiole: Leaves sessile;

Inflorescence: Panicle;

Peduncle: Branched panicle with up to ten branches; smooth, glabrous; main stems vertical, branches at about 20 degrees below vertical; flowering portion to about 31.0 cm long and about 14.0 cm across; up to 350 closely arranged flowers per panicle;

Peduncle color: Nearest RHS 187A;

Flower buds about one day prior to opening: About 23.0 mm long and about 10.0 mm wide; oblong ovoid to clavate; rounded apex; basal about 7.0 mm long narrowed to a tube about 3.0 mm diameter, with rounded base;

Bud color: Dorsal unopened petal portion between RHS N80A and RHS N80B, ventral petal portion nearest RHS 155D distally and proximally lighter than RHS 77D;

Flowers: Zygomorphic; perfect; bilabiate with upper and lower lip gamopetalous in about basal 18.0 mm; about 23.0 mm long and about 14.0 mm across and 16.0 mm tall; face opening to nearly flat; lasting about five to seven days;

Flower attitude: Mostly outward;

Flower fragrance: None detected;

Corolla: Glandular abaxial, glabrous adaxial dorsal petal and pubescent on adaxial ventral petal; bilabitate; dorsal petal with three lobes; ventral petal with two lobes; ventral petal lobes about 6.0 mm long and 6.0 mm across at fusion with rounded apices; two dorsal petal side lobes about 6.0 mm long and about 6.0 mm across, center lobe about 5.0 mm long and 5.0 mm across; all lobes with rounded apices; tube about 7.0 mm long and 3.0 mm diameter at base; throat about 10.0 mm long and face about 9.0 mm diameter, fused in basal 20.0 mm; lobes with rounded apex and entire margin;

Corolla color: Abaxial basal 2.0 mm nearest RHS 152D, abaxial tube between RHS N80B and RHS N80A, abaxial face nearest RHS N80B; adaxial basal 1.0 mm nearest RHS 145C, tube nearest RHS N78B, adaxial tube center nearest RHS N78B, adaxial ventral throat and three lobes lighter than RHS 77D, adaxial upper throat and dorsal lobes nearest RHS N80B proximally and N80D distally;

Gynoecium: One pistil; about 20.0 mm long;

*Style*.—About 17.0 mm long and less than about 0.5 mm diameter; color or mature flower between RHS 70A and RHS 71A distally lightening to nearest RHS 71D proximally.

*Stigma*.—Oblong, about 0.5 mm wide and about 0.7 mm long; color nearest RHS 155D.

Androecium: Four; didynamous; slightly curved;

*Filaments*.—About 20.0 mm long and about 0.8 mm in diameter; color nearest RHS 151A in basal 2.0 mm, distally nearest RHS 155D.

*Anther*.—Elliptic; dorsifixed; longitudinal; about 3.0 mm long and 2.0 mm across, versatile; color nearest RHS 202A dorsal and nearest RHS 155D ventral.

*Staminode*.—One; bearded pubescence to about 2.5 mm long on distal 12.0 mm of dorsal side.

*Staminode color*.—White NN155B on ventral side; bearded pubescence variable with both RHS 187A and RHS 162A.

*Pollen*.—Abundant; color nearest RHS 155D.

Calyx: Stellate, campanulate, fused at base; not adpressed to corolla; about 7.0 mm long and about 9.0 mm across;

Sepals: Five; lanceolate, narrowly acute apex and fused base, entire margin; to about 1.5 mm wide above fusion point and 7.0 mm long; glabrous abaxial and adaxial;

Sepal color: Abaxial color abaxial and adaxial nearest RHS 187A;

Fruit: Septicidal capsule; ovoid with acute apex and rounded base; about 10.0 mm long and 5.0 mm across; color as developing nearest RHS 187A and with maturity nearest RHS 177A;

Seed: Irregular; flattened, dried; about 1.0 mm long and about 1.0 mm diameter; color between RHS 200A and RHS 202A; Hardiness to at least U.S.D.A. zones 4 to 9; the new plant performs best with good drainage and is resistant to drought once established;

*Pest and disease resistance*.—Resistance beyond that typical of beardtongue plants has not been observed. No other susceptibility or resistance to diseases or pests has been observed except that which is common to *Penstemon*.

It is claimed:

1. A new and distinct cultivar of hardy beardtongue plant, *Penstemon* 'Midnight Masquerade' as herein described and illustrated.

* * * * *